United States Patent [19]

Shoher et al.

[11] Patent Number: 4,814,008

[45] Date of Patent: Mar. 21, 1989

[54] DENTAL MATERIAL

[76] Inventors: Itzhak Shoher, 50 Shlomo-Hamelech St., Tel-Aviv, Israel, 64386; Aharon E. Whiteman, 13, J. L. Perez St., Petach-Tikvah, Israel, 49206

[21] Appl. No.: 723,063

[22] Filed: Apr. 15, 1985

[51] Int. Cl.$^4$ .................................................. B22F 7/08
[52] U.S. Cl. ...................................... 75/252; 433/207; 75/255
[58] Field of Search ........................... 75/251, 252, 255; 433/200.1, 228.1, 207; 420/507–510

[56] References Cited

U.S. PATENT DOCUMENTS

| | | | |
|---|---|---|---|
| 324,650 | 8/1885 | Buatt | 420/527 |
| 3,502,466 | 3/1970 | Vickery | 75/208 |
| 3,834,024 | 9/1974 | Kochavi | 72/8 |
| 4,273,580 | 1/1981 | Shoher | 75/165 |
| 4,295,941 | 10/1981 | Lustgaiten | 433/207 |
| 4,461,618 | 7/1984 | DeLuca et al. | 433/200 |

*Primary Examiner*—Christopher W. Brody

[57] ABSTRACT

A dental material of a metal composition for reinforcing the metal framework of a dental restoration comprising an aggregate combination of metal particles including a first high fusing temperature precious metal component and a second low fusing temperature precious metal component. The particles of the first component are in a proportion of 1–15% by volume of the total composition and have a particle size at least about five times larger than the particle size of the second component.

12 Claims, No Drawings

DENTAL MATERIAL

This invention relates to a dental material of metal composition and to a method for reinforcing the metal framework of a dental restoration using the dental material of the present invention.

BACKGROUND OF THE INVENTION

In crown and bridge prosthodontics, a wide diversification of retainers and pontics can be used in various combinations for constructing a bridge. A ceramic to metal restoration uses a framework of metal as reinforcement for the crown and bridge upon which is applied a fired on coating of a ceramic material such as porcelain. The framework of metal may either be cast or formed from prefabricated units of preformed copings and pontics. In accordance with the present practice, a framework may be altered by soldering but otherwise cannot be modified or reinforced without involving investment and casting operations. Present practice is limited because of the unavailability of commercial materials with which to build up or extend the framework. To reinforce a framework without investment and casting requires adding material to the framework which upon heat treatment will become an integral part of the framework. The material must be capable of being molded into a desired shape and must be self-supporting in the molded configuration as well as capable of retaining the shape in which it was molded under heat treatment. To be able to shape the material into a desired configuration, the material should be relatively soft and workable. Under heat treatment, the material should solidify into a rigid mass of metal without losing the shape in which it was molded prior to heat treatment. The material should fuse to the metal framework and should have a hardness characteristic of at least equal but preferably greater than the hardness of the material before heat treatment.

Such a material could be used, for example, to build up a cervical shoulder around a retaining member at the gingival margin without the need for investment or casting. For example, a finishing shoulder can be formed around a prefabricated metal coping which was preformed without a shoulder margin. The finishing shoulder can be molded into any shape by the dental technician. Likewise, the material can be used to build metal cusps upon a metal coping before ceramic porcelain is added to provide buccal and/or lingual cusp reinforcement. The material may also be used to strengthen joints at predetermined locations in the framework or for general bridgework repair. The latter is, at present, relatively impossible. Heretofore, the dentist and dental technician were essentially limited to use of cast dental structures and to materials useful as solders or fluxes. Neither the conventional solder nor flux is capable of being molded into a self supporting configuration nor is either material capable of retaining a shape under heat treatment. Soldering alloys are, in fact, designed to melt and flow freely under the heat of a soldering flame and function to joint metals by fusion. A flux is a non-oxidizing agent.

SUMMARY OF THE INVENTION

A dental material of metal composition has been discovered in accordance with the present invention which can be applied to a metal framework, molded into a desired self supporting shape and upon the application of heat treatment fused to the framework and solidified into a rigid mass of metal retaining the shape in which it has been molded. In one embodiment of the present invention, the dental material comprises an aggregate combination of metal particles adapted to be subjected to heat treatment in a predetermined range for forming a dental reinforced metal restoration comprising at least a first and second precious metal or metal alloy, with the particles of the first precious metal or metal alloy being in a proportion of from 1-15% by volume of the total composition and having a particle size substantially larger than the corresponding particle size of the second precious metal or metal alloy and a melting temperature above the heat treatment temperature. The particles of the second precious metal or metal alloy are adapted to substantially melt and flow around said first precious metal in response to such heat treatment.

In an alternate embodiment of the present invention, the dental material comprises an aggregate combination of metal particles which are adapted to be subjected to heat treatment in a predetermined temperature range including a high fusing temperature component having a melting point above the heat treatment temperature and a low fusing temperature component adapted to substantially melt during the heat treatment and with the low fusing temperature component comprising a first precious metal substantially of gold and a second precious metal or metal alloy adapted to interact with the first precious metal during heat treatment to form an alloy which is substantially harder than that of the first precious metal or metal alloy. The particle size of the high fusing temperature component should be substantially larger than the particle size of the second precious metal of the low fusing temperature component and in a proportion of from 1-15% by volume of the total composition.

The method for reinforcing a metal framework in the preparation of a dental restoration in accordance with the present invention comprises forming a material composed of a composition of metal particles having in combination, at least a first and second precious metal with the particles of the first precious metal being in a proportion of from 1-15% by volume of the total composition and having a particle size substantially larger than the corresponding particle size of the second precious metal and a melting temperature substantially above the melting temperature of the second precious metal; adding the material to the metal framework; molding the material into a predetermined shape; and sintering the molded material at a temperature to cause the material to fuse to the framework and to cause the second precious metal particles to flow between the particles of the first precious metal. A ceramic material may then be applied to the reinforced framework in a conventional fashion and fired in a furnace to form a ceramic to metal dental restoration.

DECRIPTION OF THE PREFERRED EMBODIMENTS

Broadly the dental material of the present invention is a composition of metal particles which can be molded into a desired self-supporting shape for forming a dental reinforcement upon heat treatment. The dental material of the present invention will fuse to the dental framework upon heat treatment and solidify into a rigid mass retaining the shape in which it was molded. The dental material is composed of a composition of metal particles containing at least a first and second metal or metal alloy. The particles of the first metal should have a particle size at lest equal but preferably greater than the particles of the second metal and should represent from about 1 to 15% by volume of the total composition of the dental material. The melting temperature of the first metal should also be substantially higher than the melting temperature of the second metal and substantially higher than the desired heat treatment temperature for the material. Under heat treatment, the particles of the second metal should melt and intermesh with the particles of the first metal to retain the shape given the material prior to heat treatment.

A binder or other suitable carrying vehicle may be added to the composition of metal particles in forming the dental material of the present invention to give the material a paste or putty-like constituency. This should make the material easier to work with. A binder should be selected which will volatize during heat treatment without leaving a residue. Any suitable organic resinous or synthetic resinous material is acceptable such as, for example, ethylene or polyethylene glycol.

The composition of metals forming the dental material should be bio-compatible for use in the mouth. Accordingly, precious metals and precious metal alloys are preferred although not essential. The precious metals may also be used in combination with non-precious metals. In the foregoing embodiment of the invention, the particles of the first metal are represented by a high fusing temperature metal composition primarily composed of a combination of from 0 to 100% platinum and from 100 to 0% palladium. Gold may be added to the high fusing temperature metal composition to increase the affinity of the particles of the first metal to the second metal. The particles of the second metal are represented by a low fusing temperature metal composition substantially or entirely of gold. The preference for gold as the major constituent of the dental material is based on its known characteristics of workability, non-oxidizing property and its color.

The size of the particles of the high fusing temperature metal component and its volume proportion in the total composition relative to that of the low fusing temperature metal component is an essential characteristic of the present invention. Best results are achieved when the particle size of the high fusing temperature component is at least equal to the particle size of the low fusing component but preferably about 5–10 times larger than the particle size of the low fusing component. In addition, the high fusing component should be in a proportion of from 1-15% by volume of the total composition. The shape of the particles of the high fusing component is considered important to the present invention but is not a critical characteristic. The shape of the high fusing component particles will influence its particle size and volume requirements in the total composition. The function of the high fusing temperature particles are to provide multiple sites to attract, hold and retain the low fusing temperature particles under heat treatment. During heat treatment, the low fusing temperature metal particles melt and flow into the intertices between particles of the high fusing temperature component. The high fusing metal particles attract the low fusing component and contain the low fusing metal to preserve the molded shape. The attraction may be attributable to adsorption and surface tension which may also be responsible for containing the metal.

The shape of the high fusing component particles and their size relative to the low fusing component also appears to affect the affinity of the low fusing component to the high fusing component. Irregularly shaped particles appear to function best. An irregular shape allows the particles of the first metal to interlock in a random fashion and form a mesh for attracting and retaining the low fusing metal under heat treatment. The low fusing metal flows into the open network formed by the particles of the high fusing temperature component. Any irregular shape is acceptable although particles in the form of strips preferably with a spiral or corkscrew shape are preferred.

Although the material of the present invention is a composition of metal particles, the method of forming the particles is not critical to the present invention nor must the high fusing component particles be physically separated from the low fusing component particles. For example, each particle in the composition may be a composite of a high fusing temperature component and a low fusing temperature component cladded to one another or with one encapsulating the other. Cladded particles may be formed, for example, from multiple layered sheets which may have been laminated. Various other known deposition processes may also be used to form layered sheets or to encapsulate the particles one within the other including, for example, electrodeposition and cathode sputtering. Where the metal particles are cladded to one another the proportion of the high fusing component to the low fusing component in the total composition would be based on the difference in the thickness between the cladded metals. The particles do not have to be homogeneous in size or shape.

As earlier stated, the proportion by volume of particles of the high fusing metal component to the total composition is a critical characteristic of the present invention. The high fusing metal component should be in a proportion of from 1-15% by volume of the total composition with 1-10% by volume being preferred and 2-4% by volume being optimum. An insufficient proportion of particles of the high fusing temperature component will not provide sufficient sites for attaching and containing the low fusing metal under heat treatment. This would seriously affect the ability of the dental material to retain the premolded shape it was given prior to heat treatment. An excess volume of particles of high fusing temperature metal in the total composition will not allow sufficient shrinkage of the metal mass to occur in response to heat treatment. The mass of metal must be permitted to shrink to avoid forming voids and bubbles during heat treatment.

Heat treatment is applied by sintering the material under a Bunsen burner or in a furnace at a temperature below 1200° C. and preferably between about 1075° C. to 1175° C.

A more preferred embodiment of the invention is to form a dental material composed of an aggregate of metal particles comprising in combination three precious metals or metal alloy components. This embodiment is an extension of the teaching of the first embodiment employing a high fusing temperature component of precious metals or metal alloy particles in combination with a low fusing temperature component of precious metals or metal alloy particles. The high fusing temperature component is intended to provide multiple sites to attract and hold the low fusing temperature component in position under heat treatment. The low fusing temperature component is made up of particles of a first and second precious metal with the first precious metal component adapted to melt at the heat treatment temperature and with the second precious metal component adapted to interact with the first precious metal component during heat treatment to form an alloy with a hardness characteristic above the hardness characteristic of the first precious metal component. The particles of the second precious metal should provide substantial surface contact area for the first precious metal in order to maximize its interaction. Accordingly, the particles of the second metal should be smaller in size than that of the first metal. The preferred composition of metal particles comprises a low fusing temperature component including a first metal of up to 100% gold and a second metal containing primarily gold in addition to other precious metals and/or non-precious metals which will interact with the first metal component upon heat treatment to improve the hardness characteristic of the total material and a high fusing temperature component composed of a precious metal composition substantially of either platinum or palladium or a combination thereof.

The size of the particles of the high fusing temperature component should be at least equal in size to the low fusing temperature component but preferably at least 5-10 times larger than the size of the particles of the second metal in the low fusing temperature component. In the preferred composition, as indicated above, the size of the high fusing temperature particles may be, for example, about 200 microns whereas the size particles of the second metal in the low fusing temperature component may be in a range of about 20-30 microns.

To maximize the degree of bonding between the metal composition and the dental framework, it is desirable, although not essential, to include a small percentage of a chloride such as silver chloride in an amount of up to about 1%. The minor chloride addition also acts as a flux and appears to improve the ability of the second metal in the low fusing temperature component to flow during heat treatment.

The preferred composition for the dental material of this embodiment comprises a low fusing temperature component consisting of a first and second precious metal composition with the first metal being essentially of pure gold and the second metal a composition of gold, platinum and palladium with minor additions of other constituent elements. The elements in the second metal may be, for example, in the following relative proportion by volume: 15-20% Pt; 3-6% Pd, remainder gold with up to 3% total of other minor elements. The high fusing temperature component should be primarily of platinum or palladium or a combination thereof.

The volume percent of the high fusing temperature component in the dental material should preferably be from 1 to about 10% with 2-4% being optimum. In the low fusing temperature component, the second metal represents between 5-15% of the total dental material composition with about 10% being preferred and with the first metal component representing the remainder.

As earlier mentioned, a binder may be added to the composition to give it a paste-like clay constituency which should make the material easier to work with. The material is added to a metal framework, e.g., the coping, to add reinforcement to the structure. The material may be applied to the framework by a brush or spatula and molded by hand. It is, however, preferred that a conventional condensing instrument, such as an ultrasonic vibrator, be used to symmetrically build up and condense the material to the framework. After molding the material to the desired shape, the structure is placed in a furnace and sintered for between about 5 to 10 minutes. The sintering operation causes the added material to fuse to the framework and solidify into a rigid mass retaining whatever shape it was given prior to heat treatment. The shape of the material will depend upon the reinforcement function which the material is intended to provide. Where the material is used to provide a cirvical margin around a coping, it will be given the shoulder design preferred by the technician. Where a cusp is to be added, the shape and size of the added cusp will depend on the tooth to be restored. The amount of shrinkage that will occur in the furnace will depend upon the volume percent of the high fusing temperature component in the composition and whether the material was condensed with an ultrasonic vibration.

After the reinforced understructure is removed from the furnace the porcelain veneer material is coated and fired in a conventional manner.

It should be understood that the invention is not to be construed as limited to any given application for the materal. The material may, for example, be added to the metal framework after the porcelain has been fired. If, for example, a crown is too short at the margin this material may be used to extend the crown. Accordingly, the word "reinforce" is not to be construed as being limited to an improvement in framework strength or support but is instead to be given a much broader definition so that it specifically encompasses the idea of increasing the size and physical dimensions of the framework by simply adding to or extending the framework. In the same manner the material of the present invention may be used to fill a space between adjacent teeth upon which a fired on ceramic veneer may be applied, if desired.

What we claim is:

1. A dental material for reinforcing the metal framework of a dental restoration comprising an aggregate combination of metal particles which are adapted to be subjected to heat treatment in a predetermined temperature range, said metal particles including a first high fusing temperature precious metal component having a melting point above said heat treatment temperature and a second low fusing temperature precious metal component adapted to substantially melt during said heat treatment and with the particles of said fist component being in a proportion of from 1-15% by volume of the total composition and having a particle size at least about five times larger than the particle size of the second component.

2. A dental material as defined in claim 1 wherein said low fusing temperature component is composed of up to 100% gold.

3. A dental material as defined in claim 2 wherein said high fusing temperature component is selected from the group comprising platinum and palladium.

4. A dental material as defined in claim 1 wherein the particle size of said low fusing temperature component is in a range of about 20-30 microns.

5. A dental material as defined in claim 1 wherein said low fusing temperature component comprises a composition of a first and second metal or metal alloy.

6. A dental material as defined in claim 5 wherein said first metal forms an alloy with said second metal during heat treatment having a hardness above the hardness of said first metal.

7. A dental material as defined in claim 6 wherein said first and second metals are precious metals with said first metal being composed of up to 100% gold.

8. A dental material as defined in claim 7 wherein said second precious metal is selected from the group comprising platinum and palladium in combination with gold.

9. A dental material as defined in claim 8 wherein the composition of said second precious metal comprises between about 0-20% Pt, 0-20% Pd, remainder gold.

10. A dental material as defined in claim 9 further comprising a minor addition of silver chloride.

11. A dental material as defined in claim 3 wherein said high fusing component has an irregular shape.

12. A dental material as defined in claim 11 wherein said first and second components are cladded to one another forming cladded particles, with the proportion of high fusing to low fusing being based on the differences in thickness between the cladded metals.

* * * * *